United States Patent [19]

Daniel, Jr.

[11] 4,094,066
[45] June 13, 1978

[54] SURGICAL RAZOR BLADE WITH INTEGRAL GUARD

[76] Inventor: Donald S. Daniel, Jr., 102 Windsor Way, Richmond, Va. 23221

[21] Appl. No.: 775,475

[22] Filed: Mar. 8, 1977

[51] Int. Cl.² .............................................. B26B 21/54
[52] U.S. Cl. ...................................... 30/346.58; 30/77
[58] Field of Search .................. 30/346.56, 346.58, 77, 30/78, 53

[56] References Cited

U.S. PATENT DOCUMENTS

| | | | |
|---|---|---|---|
| 1,846,622 | 2/1932 | Thompson | 30/346.58 |
| 3,505,734 | 4/1970 | Iten | 30/346.58 |
| 3,555,682 | 1/1971 | Laszlo | 30/346.56 |
| 3,675,325 | 7/1972 | Michelson | 30/346.58 |
| 4,037,322 | 7/1977 | Bresler | 30/53 |

Primary Examiner—Jimmy C. Peters
Attorney, Agent, or Firm—Harold L. Stowell

[57] ABSTRACT

A surgical razor blade intended for one time use in shaving hair has an integral guard in the form of spiral windings of a fine flexible thread with the windings extending in uniformly spaced fashion around the blade cutting edge. The thread has a diameter within the range of 0.2 mm (0.0078 inches) to 1.0 mm (0.039 inches) and the spacing between adjacent windings of the thread is within the range of 1.0 mm (0.039 inches) to 4.0 mm (0.157 inches).

1 Claim, 5 Drawing Figures

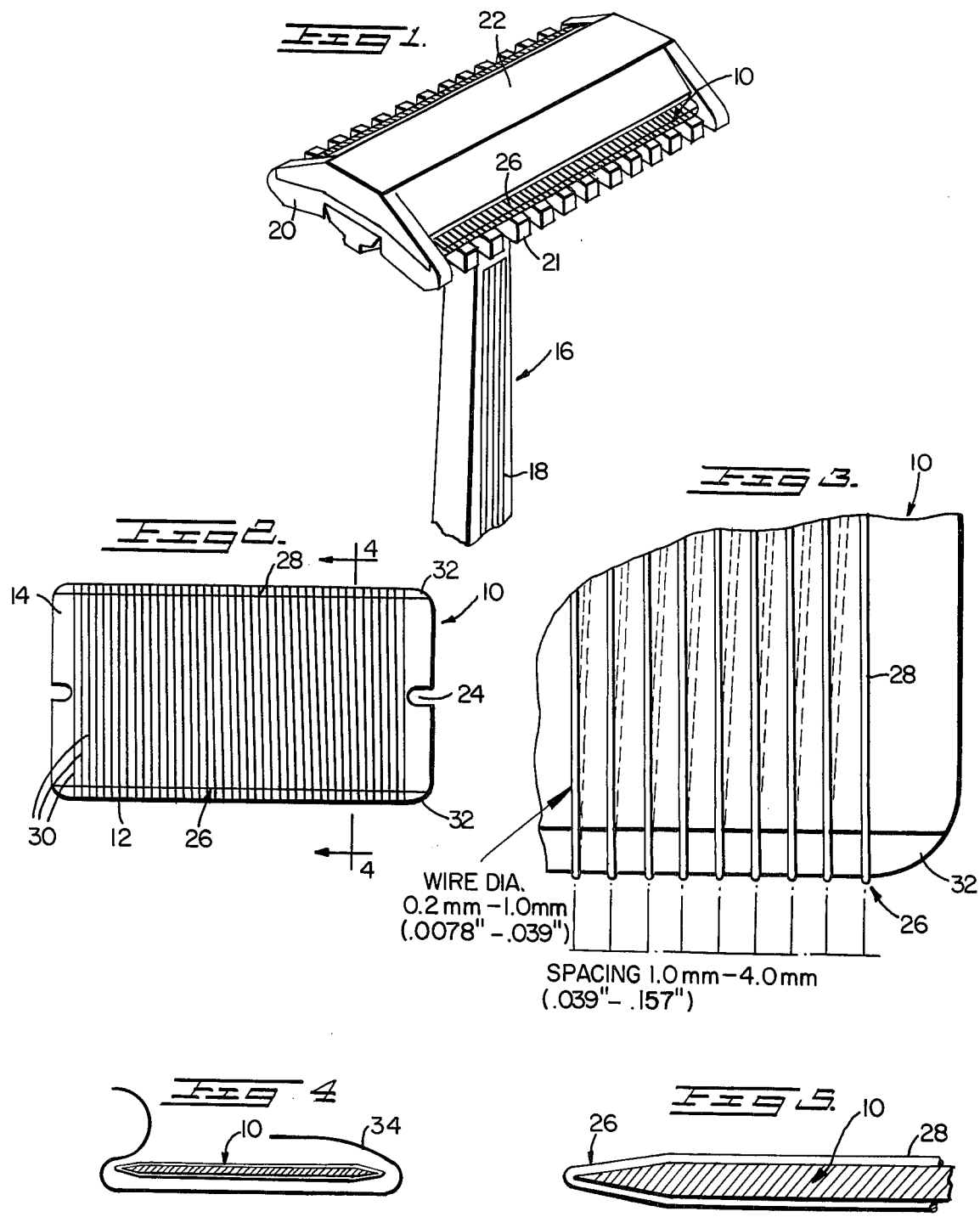

SURGICAL RAZOR BLADE WITH INTEGRAL GUARD

BACKGROUND OF THE INVENTION

1. Field of the Invention

The present invention generally appertains to new and novel improvements in cutting blades and is particularly directed to a new and novel razor blade for use in surgical shaving.

2. State of the Art

The provision of razor blades with an integral or self-contained guard in the form of spiral windings of a flexible wire is well-known in the art. One of the earliest prior art proposals can be found in U.S. Pat. No. 1,035,548 issued on Aug. 13, 1912 to Dickenson. In such patent, a straight razor is disclosed with the blade thereof having a wire spirally wound therearound so as to form some type of guard. As is clear from FIG. 1 of such patent, the windings are widely spaced along the cutting edge of the blade on an unspecified arrangement.

There is no suggestion in such patent of any criticality in such spacing of the windings of the wire nor of the diameter of the wire.

More recently, U.S. Pat. No. 3,505,734 was issued to Iten on Apr. 14, 1970. The razor blade of Iten follows the general teachings of Dickenson but complements the same in establishing a criticality between the spacing of the windings of the wire and the wire diameter dimensions. Iten recognizes the importance and criticality of the diameter of the wire or thread and the spacing between adjacent turns or windings of the wire or thread.

The razor blade of the Iten patent is primarily intended for shaving terminal hairs on the facial areas of the body and the specified critical values of the spacing of the windings of the thread are based on the normal facial hair sizes.

In this regard, it must be recognized that the epidermis of the face is dissimilar from the epidermis of the other portions of the body, such as the abdomen or pubic areas. The epidermis of the face can withstand greater irritation than the epidermis of the abdomen or other areas of the body, having regard to shaving of the hairs. The facial areas are shaven on a daily or regular schedule, whereas other areas of the body, being prepared for operations, are shaven generally on a one time only basis. Also, the cross-sectional shape and size of the hairs on the facial areas are very different from the cross-sectional shape and size of the hairs found on the body.

Because of such differences, the razor blade of the Iten patent would not be particularly usable for preparation of an operative site or preparation of a body area at a proposed intraveneous or intraarterial catheter or injection location even though Iten has suggested such use.

SUMMARY OF THE INVENTION

The primary object of the present invention is to provide a surgical razor blade that can be employed by untrained hands for removal of the long, previously unshaven body hairs without cutting or otherwise lacerating the skin.

The razor blade of the present invention is intended for sole use in removing hair shafts from generally previously unshaven areas of the body for surgical purposes. The blade is intended for use in preparation of an operative site, prior to the repair of a wound, or at a proposed intravenous or intraarterial catheter or injection location or the like. The surgical razor blade is intended for single use for sterile purposes and is designed to all but eliminate the occurrence of a laceration in the body area being shaven. The elimination of a laceration is important because the presence of blood at a cut site can act as the locus of infection as blood is an ideal culture medium. Secondly, from a psychological standpoint the pain of a nick or cut would tend to aggravate a patient's anxiety.

Shaving the body skin lessens the likelihood of wound infection because it removes the hair to which bacteria may cling; however, extreme care should be taken that the skin is not cut during shaving. The skin should be lubricated, as with hexachlorophene, and the hair shafts should be shaven in the direction in which they grow. Such skin preparation may be carried out in the operating room but usually is done in the patient's room prior to transport to surgery. In general, the area to be shaven should be more extensive than actually required for the incision. This will allow for a margin of safety and will prevent the skin adjacent to the wound from being a source of contamination during draping. Then, too, if it should be necessary to extend the incision, such can be safely carried out.

The surgical razor blade of the present invention has its cutting edge or edges encompassed by uniformly spaced windings of a flexible thread with the important and critical factors, having regard to the intended surgical usage of the blade, being that the thread diameter is within the range of 0.2 mm (0.0078 inches) to 1.0 mm (0.039 inches) and the spacing between adjacent windings of said thread is in the range of 1.0 mm (0.039 inches) to 4.0 mm (0.157 inches).

The thread size, if any smaller than 0.2 mm in diameter, would tend to permit the very act against which it is designed, especially in areas of the body where angles are sharp and varying. Should the spacing between the threads be narrower than 1.0 mm the larger body hairs could not be readily severed. Either a thread diameter larger than 1.00 mm or a thread spacing wider than 4.0 mm would render the surgical razor blade too cumbersome for use by untrained hands. The closeness of the shave is not the major aim, rather one wishes removal of the long, previously generally unshaven body hairs.

Ideally, the surgical blade could be manufactured in several thread sizes and thread spacings, for example, small thread diameter 0.2 to 0.4 mm and spacing 1.0 to 2.0 mm; medium thread diameter 0.4 to 0.7 mm and spacing 2.0 to 3.0 mm; and large thread diameter 0.7 and 1.0 mm and spacing 3.0 to 4.0 mm for use in fine, medium and course hair areas.

Blades best used for preparation of an intravenous site of small diameter may not be as suitable when one is preparing a larger coarser area such as the pubic region. Thus, each specific surgical application has a preferred thread diameter and thread spacing.

In conjunction with the critical spacing and diameter of the guard thread or wire, an additional safety feature of the present invention includes the rounding of the ends of the cutting edge of the surgical razor blade, or in the instance of a double edge blade, the rounding of the ends of both edges. By rounding such ends, sharp corners, regardless of the angle of such corners, are eliminated and, thereby, a further source of an inadvertent cut or nick or the patient's skin is eliminated.

The thread or wire is formed from any flexible material that has the capacity to conform to the configuration of the blade to which it is fixed. In addition, the thread or wire should be formed of a material that possesses the capability to be able to be pressed against the cutting edge of the blade, under pressure in normal shaving contact with the patient's body, without causing the windings to be cut. Suitable materials are fine metallic wires or synthetic spun wires or filaments. The thread or wire is looped around the blade in spiral fashion and the windings may be fastened to the blade in an inconspicuous manner, preferably by a conventional adhesive. But, obviously, other fastening means may be used in adhering selected or all of the thread windings to the body of the blade.

The thread is wrapped around the blade in a manner so as to produce a plurality of spiral windings with spacing between adjacent windings of the thread being uniform and in the range of 1.0 mm (0.039 inches) to 4.0 mm (0.157 inches). The specified spacing is critical as is the diameter of the thread which must be within the range of 0.2 mm (.0078 inches). to 1.0 mm (0.039 inches). Because of the specified critical spacing of the windings, the long and larger diameter hairs are combed into contact with the cutting edge which because of the specified critical diameter of the thread cannot nick or cut the body even when such areas are being treated by unskilled hands and such areas are of angular nature.

Since it is important that the surgical razor blade be sterile and since it is intended to be used on a one time only basis, the blade may be dispensed in a suitable paper or plastic wrapper that can be removed by the attendant prior to use of the blade on a patient.

BRIEF DESCRIPTION OF THE DRAWING

FIG. 1 is a perspective view in elevation of a surgical razor blade mounted in a holder.

FIG. 2 is a plan view of the surgical razor blade.

FIG. 3 is an enlarged detailed view of one corner of the blade.

FIG. 4 is a cross-sectional view taken substantially on lines 4—4 of FIG. 2 and showing fragmentarily the wrapper for the blade.

FIG. 5 is an enlarged detailed illustration of one winding and its association with the cutting edge of the blade.

DESCRIPTION OF THE PREFERRED EMBODIMENT

Referring now particularly to the accompanying drawing, numeral 10 generally designates a double cutting edge razor blade which is extremely thin, for example, on the order of less than 0.010 of an inch in thickness. the blade has opposing cutting edges 12 and 14, but, as can be appreciated, only a single cutting edge is required. In this respect, also, the particular formation of the blade 10, as illustrated in the drawing, is for exemplary purposes only since the blade can be of any form and design.

As illustrated, the double edge blade 10 is intended to be supported by a suitable holder 16 which is shown in FIG. 1. Such holder generally comprises a handle 18 that supports a bottom plate 20 on which a top plate 22 is adapted to be attached with the blade 10 being locked therebetween by virtue of connection means between the top and bottom plates that cooperates with the notches 24 in the ends of the blade to clamp the blade between the two plate members. For surgical use, the bottom plate 20 may be provided with a comb 21.

The blade is provided with an integral guard 26 so that it may be said that the blade has a self-contained guard. Such guard is composed of a thin flexible thread of wire 28 spirally wound around the blade as shown in FIGS. 2 and 3 with the windings 30 passing over the cutting edge or edges of the blade. The thread or wire can be of any flexible material that will conform to the blade configuration and that will be capable of being pressed against the cutting edge or edges of the blade under pressure in normal shaving operations without being severed. Steel, nylon or other materials may be used for the thread or wire. The thread is preferably made unitary in its spiral windings with the blade by any suitable attachment means, such as an adhesive.

The ends 32 of the cutting edges are rounded so that no sharp angular corners are present. Also, because of its intended use, the blade 10 and/or blade and holder are wrapped in a plastic or paper covering 34 of the type which will permit sterilization.

The firm flexible wire or thread 28 coiled around the blade in its spiral turns 30 must have a diameter within the range of 0.2 mm (0.0078 inches) to 1.0 mm (0.039 inches) and the uniform spacing between adjacent windings 30 of the wire or thread must be in the range of 1.0 mm (0.039 inches) to 4.0 mm (0.157 inches) in order that the razor blade 10 can be used by an inexperienced person to shave the hairs on the patient's body without inflicting a nick or cut on the skin surface.

It can be appreciated that the design and form of the blade 10 are critical, so different embodiments of the invention can be realized as long as the specified critical values of the spacing of the thread windings and the diameter of the thread are maintained.

What is claimed is:

1. A surgical razor blade with an integral guard for its cutting edge in the form of a plurality of spiral windings of thread being of flexible material capable of being pressed against the blade cutting edge under pressure in shaving contact with the normally unshaven areas of the skin without severance of the thread, said thread having a diameter within the range of 0.2 mm to 1.0 mm, said windings extending around the cutting edge of the blade in a uniformly spaced manner and the spacing between adjacent windings being selected from the group consisting of 1.0 to 2.0 mm; 2.0 to 3.0 mm and 3.0 to 4.0 mm, and wherein said blade is sterile and is packaged in such condition for one time use only.

* * * * *